United States Patent
Sarama et al.

(10) Patent No.: US 9,290,752 B2
(45) Date of Patent: Mar. 22, 2016

(54) PROCESS FOR ENHANCING THE AMYLASE INHIBITORY EFFICACY FROM PHASEOLUS VULGARIS EXTRACTS

(71) Applicant: Sunny Delight Beverages Company, Cincinnati, OH (US)

(72) Inventors: Robert Sarama, Loveland, OH (US); Gregory Arcuino, Cincinnati, OH (US)

(73) Assignee: Sunny Delight Beverages Co., Cincinnati, OH (US)

( * ) Notice: Subject to any disclaimer, the term of this patent is extended or adjusted under 35 U.S.C. 154(b) by 52 days.

(21) Appl. No.: 14/204,622

(22) Filed: Mar. 11, 2014

(65) Prior Publication Data

US 2014/0273157 A1  Sep. 18, 2014

Related U.S. Application Data

(60) Provisional application No. 61/779,584, filed on Mar. 13, 2013.

(51) Int. Cl.
| | |
|---|---|
| *C12N 9/00* | (2006.01) |
| *C12N 9/32* | (2006.01) |
| *C07K 14/415* | (2006.01) |

(52) U.S. Cl.
CPC ............ *C12N 9/2422* (2013.01); *C07K 14/415* (2013.01)

(58) Field of Classification Search
None
See application file for complete search history.

(56) References Cited

U.S. PATENT DOCUMENTS

| | | |
|---|---|---|
| 6,340,669 B1 | 1/2002 | Cestaro et al. |
| 2006/0147565 A1 | 7/2006 | Skop et al. |
| 2009/0042779 A1 | 2/2009 | Bollini et al. |
| 2009/0169657 A1 | 7/2009 | Berlanda et al. |

OTHER PUBLICATIONS

Layer et al. Gastroenterology. 1985, vol. 88, No. 6, p. 1895-902, Abstract Only.*
Barrett et al., Nutrition Journal, 2011, vol. 10, p. 4-10.*
International Search Report and Written Opinion dated Oct. 22, 2014 for Application No. PCT/US2014/0214/024176.
Le Better-Anton, V., et al., "Characterization and functional properties of the α-amylase inhibitor (α-AI) from kidney baen (*Phaseolus vulgaris*) seeds", Biochimica et Biophysica Acta, 1997, 1343:31-40.
Kumar, A., et al., "Affinity Precipitation of α-Amylase Inhibitor from Wheat Meal by Metal Chelate Affinity Binding Using Cu(II)-Loaded Copolymers of 1-Vinylimidazole with *N*-Isopropylacrylamide", Biotechnology and Bioengineering, vol. 59, No. 6, pp. 695-704, Sep. 20, 1998.
Pick, K-H., et al., "Proteinaceous α-Amylase Inhibitor from Beans (*Phaseolus vulgaris*)", Hoppe-Seyler's Z. Physiol. Chem. Bd. 359, S. 1371-1377, Oct. 1978.

* cited by examiner

*Primary Examiner* — Kade Ariani
(74) *Attorney, Agent, or Firm* — Frost Brown Todd LLC

(57) ABSTRACT

An improved method of purifying bean extract alpha-amylase inhibitor protein material is described. The materials purified by this process provide significantly more amylase inhibition than materials purified by other processes. In this process: (a) bean extract-derived alpha-amylase inhibitor is suspended in an aqueous solution having a pH of from about 3.0 to about 3.5; (b) a preservative is added to the solution; (c) the solution is heated to about 175 to about 195 F for about 10 to about 120 seconds; (d) the solution is cooled to about 65 to about 85 F and allowed to sit, in a non-agitated state, for about 3 to about 24 hours, such that bean extract particles settle out of solution; and (e) the supernatant, which contains the purified amylase inhibiting protein, is separated from the particles.

9 Claims, No Drawings

PROCESS FOR ENHANCING THE AMYLASE INHIBITORY EFFICACY FROM PHASEOLUS VULGARIS EXTRACTS

This application is related to and claims priority from U.S. Provisional Application No. 61/779,584, filed Mar. 13, 2013, incorporated herein by reference.

BACKGROUND

Amylase is an enzyme responsible for breaking down the main source of carbohydrates in the human diet, namely, starch. The digestion of starch begins in the mouth where alpha-amylase present in saliva hydrolyzes glucosidic bonds of starch. By the time thoroughly chewed food reaches the stomach, the average chain length of starch is reduced from several thousand to less than eight glucose units. The acid level in the stomach inactivates the salivary alpha-amylase. Further digestion of starch continues in the small intestine by pancreatic alpha-amylase, which is similar to salivary alpha-amylase.

Decreasing the absorption of carbohydrates by inhibiting the digestion of starch is a very promising strategy in the fields of, for example, weight loss and diabetes mellitus. From a dietary standpoint, it is important to target the breakdown of starch since starch is a relatively non-essential nutrient, which provides calories with little benefit.

Amylase inhibitors are derived from various sources, including vegetable albumins and leguminous plants. Currently, extracts from beans are being utilized most often as a source of amylase inhibitors.

Current methods for purification of amylase inhibitors, which include concentrating and drying beans, include the use of heat treatments and/or solvents. See, for example, U.S. Pat. No. 6,340,699, Cestaro et al, issued Jan. 22, 2002. However, the use of heat treatments and/or solvents has several drawbacks. For example, at high temperatures, certain heat sensitive components of the amylase inhibitor from beans can become degraded. As a result, the amylase inhibitor exhibits a decrease in both stability and potency. In addition, there can be environmental and health concerns associated with the use of solvents during such purification processes. For example, extraction of amylase inhibitors from beans using solvents can result in residual contamination of the extract with the toxic solvent. Furthermore, disposal of the large quantities of solvent required during purification processes can raise environmental concerns.

Examples of such amylase inhibitor purification processes are as follows:

U.S. Pat. No. 6,340,669, Cestaro et al (assigned to Hunza di Maria Carmela Marazzita S.A.S.), issued Jan. 22, 2002, describes lipoprotein complexes which comprise an amylase-inhibiting protein together with a phospholipid (such as phosphatidylcholine). These complexes are said to be useful in treating hypercholesterolemia.

U.S. Published Patent Application 2006/0147565, Skop et al (assigned to Pharmachem Laboratories, Inc.), published Jul. 6, 2006, describes the extraction and purification of amylase inhibitors from white beans using supercritical carbon dioxide processes under vacuum pressure. A method for inducing weight loss using the purified amylase inhibitors is also taught.

U.S. Published Patent Application 2009/0042779, Bollini et al, published Feb. 12, 2009, defines the use of beans, which are bred to be essentially free from phytohemagglutinin, for extracting amylase inhibitors, as well as the combination of that extract with phaseolamin. The described highly purified phaseolamin extract is said to be safe and suitable for consumption by man and animals.

U.S. Published Patent Application 2009/0169657, Berlanda et al, published Jul. 2, 2009, describes the use of hydroethanolic mixtures on suitably concentrated aqueous extracts of kidney beans to produce enriched extracts with an alpha-amylase inhibitor content having an activity between 1,000 and 1,600 USP/mg and a phytohaemagglutinin content between 8,000 and 30,000 HAU/g. It is said that this extract can be formulated for diet use at relatively low doses.

In the mouth, alpha-amylase begins the process of the enzymatic digestion of starch, a main source of carbohydrates in the human diet. Proteinaceous amylase inhibitors from Phaseolus vulgaris (white kidney bean) varieties have been known for some time. Decreasing the absorption of carbohydrates by blocking starch digestion through the inhibition of amylase can aid in the control of weight gain or diabetes mellitus. To achieve this end, methods have been developed to extract amylase inhibitors from beans in order to allow the incorporation of said inhibitors into dietary supplements. Current methods for the extraction and purification of amylase inhibitors from beans have not been totally satisfactory in terms of processes that involve harsh heat and solvent treatments which yield amylase inhibitors having impurities and/or less than full activity. U.S. Published Patent Application 2006/0147565, discussed above, describes a process for purifying the amylase inhibitor from white kidney beans that is claimed to be more potent than the amylase inhibitors derived from conventional methods employing heat and solvents. Surprisingly, it has been discovered that the amylase inhibitor extract powder as processed by the methods described in the '565 patent application can be further improved by an additional process step. The result is a clear, stable, tasteless aqueous mixture which contains the amylase inhibiting protein having a significant increase (as much as tenfold) in activity.

SUMMARY

The present invention relates to a method for purifying bean extract alpha-amylase material, comprising the steps of:
  (a) suspending the alpha-amylase material in an aqueous solution at a pH of from about 3.0 to about 3.5;
  (b) adding a preservative to the solution;
  (c) heating the solution to from about 175 F to about 195 F for from 10 to about 120 seconds;
  (d) cooling the solution to a temperature of from about 65 to about 85 F and letting the solution sit, under static non-agitated conditions, at a temperature within the defined range for from about 3 to about 24 hours to allow bean extract particles to settle out of solution; and
  (e) separating the particles from the supernatant (such as by decanting the supernatant).

All percentages and ratios given herein are "by weight" unless otherwise specified. All patents and other documents discussed herein are incorporated herein by reference.

DETAILED DESCRIPTION

The basic invention herein is a process that improves upon known processes for the purification of an alpha-amylase inhibitor from white kidney beans (Phaseolus vulgaris), that provides a product which has the following properties:
  (1) an alpha-amylase inhibitor that is up to ten times more efficacious than commercially available bean extracts,
  (2) an alpha-amylase inhibitor which is stable when maintained in an aqueous solution;

(3) an alpha-amylase inhibitor which provides a clear solution with no turbidity, settling, or bean flavor; and (4) an alpha-amylase inhibitor which can be easily incorporated into water, clear beverages, teas, etc. for the purpose of weight control.

In an effort to produce a clarifying solution of alpha-amylase inhibitor from bean extract being produced by the method described in U.S. Published Patent Application 2006/0147565, it was surprisingly discovered that the clarifying process resulted in not only clarifying the bean abstract solution, but in also increasing the amylase inhibitory efficacy tenfold over the starting material. Further, it has been observed that the inhibiting protein is more stable in that solubilized state.

In order to achieve this, the commercial bean extract powder of the process described in U.S. Published Patent Application 2006/0147565, incorporated herein by reference, was suspended in an aqueous solution containing a carboxylic acid or carboxylic acid salt (such as citric acid, malic acid and/or tartaric acid, or citrate, malate or tartrate salts) to carefully adjust the solution pH to from about 3.0 to about 3.5, such as from about 3.3 to about 3.5. A preservative, such as benzoates, sorbates, sodium hexametaphosphate (SHMP), or dimethyl dicarbonate (DMDC) was added, and the mixture was heated to from about 175 F to about 195 F, such as about 180±2 F for from about 10 to about 120 seconds, such as from about 10 to about 60 seconds (preferably from about 10 to about 20 seconds). This solution was then cooled and kept at from about 65 to about 85 F, such as from about 75 to about 85 F, to allow time for the bean extract particles to settle. An extraction time of from about 3 hours to about 24 hours, such as from about 12 to about 24 hours, under static non-agitated conditions, is needed for the extraction to occur. The supernatant is then separated from the bean extract particles (such as by decanting). The amylase inhibiting protein is found in the liquid phase. The protein can be concentrated through reverse osmosis or by gentle drying, but the protein must be maintained in solution during those processes.

The above-described process can be varied in at least the following manner:

(1) additional purification of the solution can be carried out by reverse osmosis or forms of membrane filtration;

(2) the pH of the final extract solution, as well as the specific carriers utilized, can be adjusted to from about 3.0 to about 3.5; and (3) the process can be carried out using extracts from other varieties of Phaseolus vulgaris, such as kidney beans, cranberry beans, black turtle beans, flageolet, white beans, and yellow beans, or other genetically modified cultivars.

All references, patents and patent applications cited herein are incorporated in this application by reference, unless otherwise stated.

EXAMPLE

One gram of white kidney bean extract is added to a 470 gram mixture containing 0.040 wt % sodium hexametaphosphate, 0.015 wt % citric acid, 0.009 wt % potassium sorbate, 0.009 wt % sodium benzoate and water. The mixture is heated to 180 F for 15 seconds and cooled to 85 F for 24 hours. A 5 cc aliquot sample is removed for alpha amylase inhibition testing.

Two companion control samples are also prepared and sampled for alpha amylase inhibition testing. The first control sample is prepared by adding 1 gram of white kidney bean extract to 470 grams of water, heating it to 180 F for 15 seconds and holding it at 85 F for 24 hours. The second control consists of water and all of the components (salts) as found in the rest sample.

Results of amylase testing shows that the test sample provides significantly more amylase inhibition than the control samples, on the order of 10× greater.

What is claimed is:

1. A method of purifying alpha-amylase inhibitor protein from a *Phaseolus vulgaris* bean extract material, comprising the steps of:
   (a) suspending a bean extract material derived from a *Phaseolus vulgaris* containing alpha-amylase inhibitor protein in an aqueous solution at a pH of from about 3.0 to about 3.5;
   (b) adding a preservative to the solution;
   (c) heating the solution to about 175° F. to about 195° F., for from about 10 to about 120 seconds;
   (d) cooling the solution to a temperature of from about 65° F. to about 85° F. and letting the solution sit, under static non-agitated conditions, at a temperature within that defined range for from about 3 to about 24 hours to allow bean extract particles formed therein to settle out of the solution; and
   (e) separating the particles from the solution to obtain a supernatant, wherein the supernatant contains the alpha-amylase inhibitor protein.

2. The method of claim 1 wherein, in step (a), a carboxylic acid or carboxylic acid salt is used to adjust the solution pH.

3. The method according to claim 1 wherein, in step (b), the preservative is selected from benzoates, sorbates, sodium hexametaphosphate (SHMP), dimethyl dicarbonate (DMDC), and mixtures thereof.

4. The method according to claim 1 wherein the heating in step (c) takes place for about 10 to about 20 seconds.

5. The method according to claim 1 wherein, in step (d), the solution is concentrated using reverse osmosis or gentle drying, while the alpha-amylase inhibitor protein is maintained in solution.

6. The method according to claim 1 wherein the bean extract alpha-amylase material used in step (a) is obtained by a supercritical carbon dioxide process carried out under vacuum pressure.

7. The method according to claim 1 wherein, in step (e), the particles are separated out by decanting the supernatant.

8. The method according to claim 2 wherein the carboxylic acid is citric acid or a citrate salt.

9. The method according to claim 3 wherein the preservative is sodium benzoate.

* * * * *